United States Patent [19]

Taylor et al.

[11] Patent Number: 4,936,685
[45] Date of Patent: Jun. 26, 1990

[54] METHOD AND APPARATUS FOR THE MEASUREMENT OF COLOUR PROPERTIES OF PAINT

[75] Inventors: Celia C. Taylor; Elizabeth Z. Shepherd, both of Slough; Michael L. Colclough, Weybridge, all of England

[73] Assignee: Imperial Chemical Industries, PLC, London, England

[21] Appl. No.: 396,814

[22] Filed: Aug. 22, 1989

Related U.S. Application Data

[63] Continuation of Ser. No. 232,955, Aug. 16, 1988, abandoned.

[30] Foreign Application Priority Data

Aug. 18, 1987 [GB] United Kingdom ............... 8719488
Dec. 3, 1987 [GB] United Kingdom ............... 8728279

[51] Int. Cl.$^5$ .............................................. G01J 3/50
[52] U.S. Cl. ..................................... 356/409; 356/246
[58] Field of Search ............. 356/402, 409, 410, 411, 356/414, 425, 440, 246

[56] References Cited

U.S. PATENT DOCUMENTS 4,511,251  4/1985  Falcoff et al. ............... 356/410 X

FOREIGN PATENT DOCUMENTS 0094218  11/1983  European Pat. Off. .
2525701  12/1976  Fed. Rep. of Germany .

Primary Examiner—F. L. Evans
Attorney, Agent, or Firm—Cushman, Darby & Cushman

[57] ABSTRACT

Measurement of the color properties of wet paint, such as lightness by colorimetry or photospectrometry, is carried out on a sample volume contained in a vessel and while the sample volume is subjected to shearing forces and advantageously also turbulence. The shearing and turbulence are created by a rotating disc having a spiral rib configuration on one surface which faces a window through which the measurements are made by a spectrophotometer.

15 Claims, 5 Drawing Sheets

STATIC MIXING METHOD "ON LINE" OPTION.

METHOD AND APPARATUS FOR THE MEASUREMENT OF COLOUR PROPERTIES OF PAINT

This is a continuation of application No. 232,955, filed Aug. 16, 1988 which was abandoned upon the filing thereof.

This invention relates to a method of and apparatus for measurement of one or more colour properties (e.g. lightness) of paint.

Colour measurement of paint is usually carried out by taking an aliquot of paint, applying it as a coating to a test area, allowing it to dry and then measuring one or more colour properties of the dried coating using a spectrophotometer or a colorimeter. Colour measurement by this method is very time consuming because of the paint drying time. However, other problems arise in that some paints are difficult to apply repeatedly and special precautions are required to be taken by operators when applying certain paints.

The aim within the industry for some time has been to measure the colour properties of paint in a wet state and in a way which predicts the colour of the paint when applied and dried. The theoretical benefits are mainly associated with time saving although some are associated with the increased likelihood of an automated paint plant.

However simply taking a sample of wet paint and putting it in a glass cell or spreading it for example by a lamina flow over a plate as disclosed in DE-A-2525701 and measuring its colour properties produces inconsistent results even if prior to flowing over the plate the sample is subjected to shearing forces. We have discovered that this lack of consistency arises because of the instability of wet paint to shear. This results in part from the fact that in the wet sample, pigments tend to be flocculated and tend to deflocculate on application.

An object of the invention is to provide a method and apparatus for colour measurement of wet paint that produces acceptably consistent results.

According to the invention there is provided a method for measuring a colour property of a wet paint comprising supplying a sample volume of liquid paint to a vessel, applying shearing forces to the sample volume in the vessel, the method being characterised in that the colour property of the sample volume is measured while the sample is in the vessel and during the application of shearing forces and/or within a predetermined time after the cessation of the application of shearing forces. It has been found that when a wet paint sample is subjected to shearing forces then a direct correlation can be obtained between colour properties measured in the wet paint sample under shear and colour properties measured in the applied dry coating.

The method of the invention is significantly improved if turbulence is created in the sample volume simultaneously with the application of shear forces.

Advantageously the shearing forces applied produce a shear rate in the range $10^6$–$10^{10}$ reciprocal seconds and preferably about $10^8$ reciprocal seconds.

Deriving from this method the invention also provides a colour measurement apparatus in which a device is provided for shearing a volume of wet paint within a vessel, the vessel having means for measuring a colour property of a sample volume of liquid paint within the vessel.

The means for measuring a colour property within the holder can comprise a window in the holder through which colour can be measured by, for example, a spectrophotometer, or one or more optical fibres extending from within the holder to a spectrophotometer.

In one embodiment of the invention, a volume of a paint sample is sheared at a predetermined speed for a predetermined length of time and while shearing is still in progress the selected colour property of the paint is measured using a spectrophotometer or a colorimeter. Experimental results obtained in this manner give both good repeatability and consistent correspondence with measurements of dry paint.

In another embodiment of the invention, a colour property of a volume of paint is measured immediately before, and at frequent intervals during shearing and at frequent intervals after shearing has ceased. This enables the shear stability of the measured colour property to be characterised so that the techniques used to disperse and stabilise pigments in paint can be optimised.

In a still further embodiment of the invention one or more colourants are added to a volume sample of paint while the paint is being sheared and until the colour measurements agree with predetermined specified ones, i.e. have a desired value.

In one form of apparatus according to the invention the shearing device comprises a rotatable disc disposed in the vessel (preferably with its plane substantially parallel to the window and) the disc being formed with protrusions, for example a spiral rib configuration milled or otherwise formed on one surface. In the case where the measurements of colour property are made through a window in the vessel the disc is preferably arranged with its plane parallel to the window and with the protusions formed preferably on that surface facing the window. It has been found that with a spiral configuration in addition to its shearing function the disc also creates a turbulent flow to cause movement of the paint over the glass window so that the layer of paint against the glass does not form a non-sheared lamina.

In another form of apparatus in accordance with the invention, a flow of paint is forced under pressure through the vessel which is in the form of a tube and in which a stationary shearing member extends axially, the paint after passing the shearing member then passing a window through which the colour measurements are made.

The invention will now be further described by way of example with reference to the accompanying drawings, in which.

Figure 1:
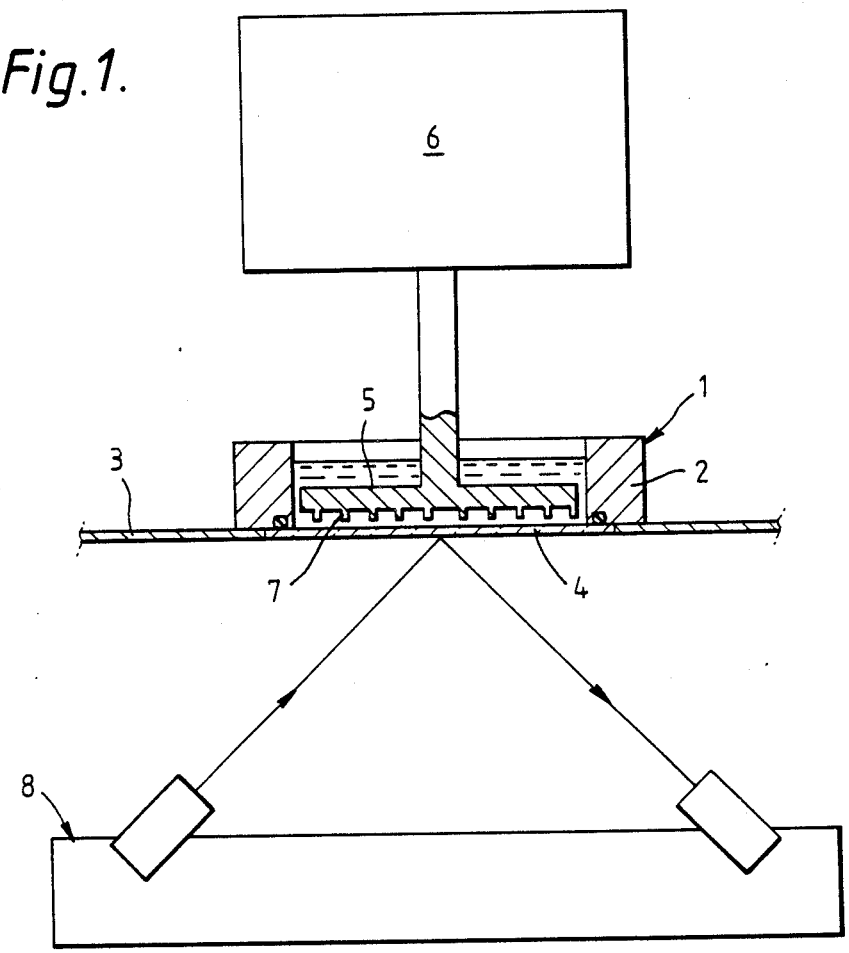
FIG. 1 is a schematic view of a first apparatus in accordance with the invention.
Figure 2:
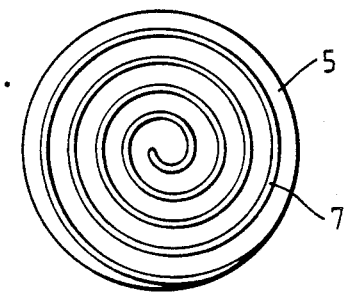
FIG. 2 is a plan view of one surface of the shearing device used in the apparatus of FIG. 1.

Referring now to FIGS. 1 and 2 of the drawings, the apparatus comprises a vessel in the form of a paint cell 1 having an annular side wall 2 and a bottom 3 in which is fitted a glass window 4 providing a viewing aperture. Disposed within the cell 1 is a paint shearing device in the form of a disk 5 which is connected for rotation to an electric motor 6. The disk 5 is disposed with its plane substantially parallel to the window 4 and on its face adjacent the window has a spiral groove milled into it as shown in FIG. 2 to provide protrusions in the form of a downwardly projecting spiral rib 7.

A spectrophotometer 8 is positioned so that it makes colour measurements through the window 4 by reflectance.

In the use of the apparatus a sample volume of paint is supplied to the cell and the device 5 set in rotation to produce the desired shear rate of about $10^8$ reciprocal seconds in the sample.

Factors affecting the operation of the apparatus are the configuration of the disk 5, its speed of rotation, the gap between it and the glass window 4 and the time for which the paint is sheared. A typical set of factors is:
1. spiral configuration as shown
2. gap 8–25 thou.
3. time of shear 5 mins.

These factors can be varied providing a number of constraints related to the properties of the paint are observed.

It has been found that in making colour measurements using this apparatus, there is a substantially straight line correlation between the colour properties of the wet and dry paint, the slope of this straight line being determined by the amount of shearing applied. Ideally the slope is 45° so that a change in for example lightness of the wet paint corresponds to an equal change in lightness of the dry paint. Thus in colour matching bulk volumes of paint to produce a predetermined dry paint coating consistently, the necessary colorant additions to the basic bulk mix to correct for any colour deficiencies can be readily calculated from the colour measurements made.

Figure 3:
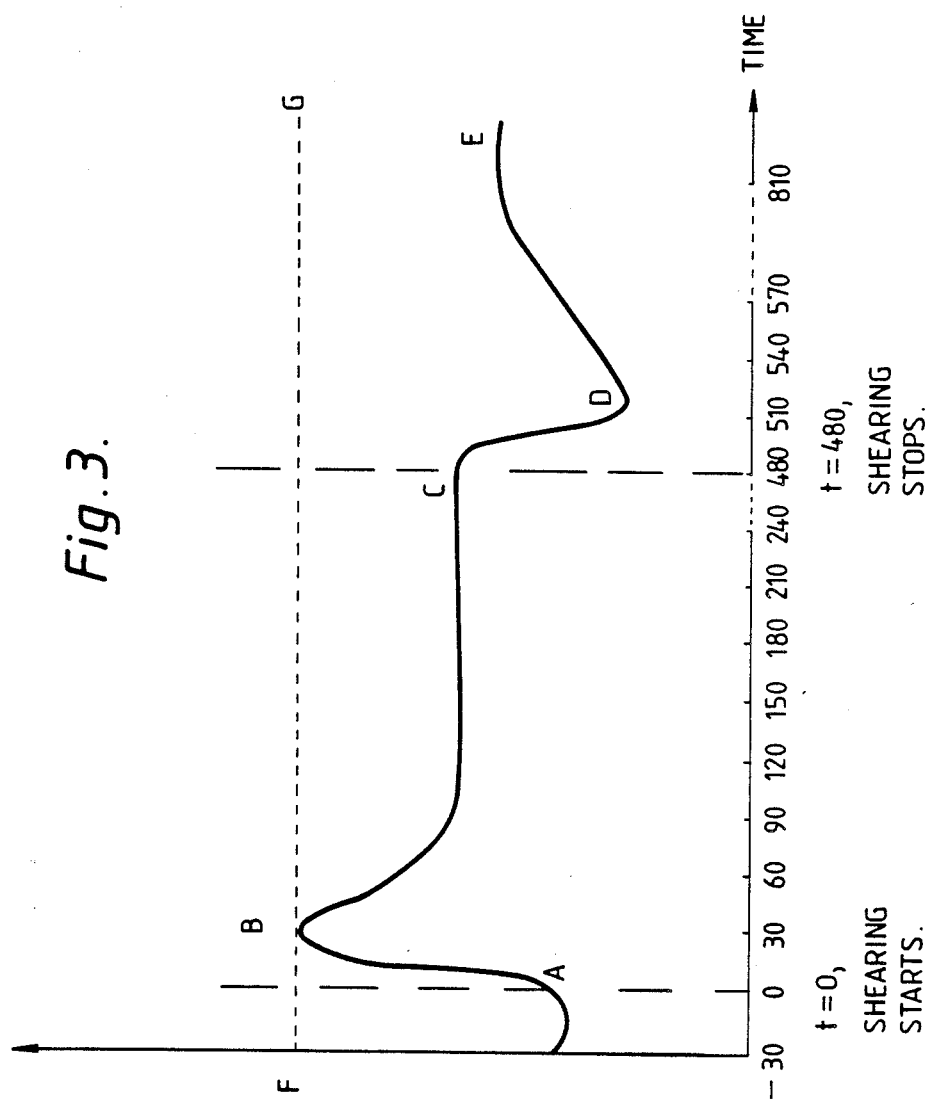
FIG. 3 shows a graph of measured colour property against time.

Referring now to FIG. 3 this is a graph showing how the sample volume varies in lightness L with Time as shearing is taking place. For consistency between one sample and another a reading of lightness would be taken on the stable plateau say after about 150 secs.

FIG. 3 also illustrates how the apparatus of FIG. 1 or similar apparatus described hereafter can be used to determine other properties of the paint which affect its colour and are therefore embraced herein by the term "colour properties".

The line FG represents a perfectly stable paint which is unaffected by shear. The line passing through points O,A,B,C,D and E represents the variation in lightness with time of a shear unstable paint during a cycle of operation of the apparatus of FIG. 1. Shearing is indicated as starting at t=o and ceasing when t=480 secs. The various portions of the line can be interpreted as follows:

OA Flooding—pigment moves to glass or air interface
AB Remixing—flooding removed as a result of shear being started
BC Deflocculation—absorbing pigments deflocculating due to shear thus increased absorption of light thus L value decreases
CD Flooding—pigment moves to air or glass interface on cessation of shear
DE—Gradual reflocculation Thus the effect of adding dispersion and stabilising agents to the paint can be observed.

In FIG. 3 the Y axis represents lightness, but it could, for reflectance at a single wavelength, represent any of the following:

| | |
|---|---|
| X | |
| Y | } tristimulus coordinates |
| Z | |
| R | |
| G | |
| B | |
| L | |
| a | } CIELAB coordinates etc. |
| b | |

Figure 4:
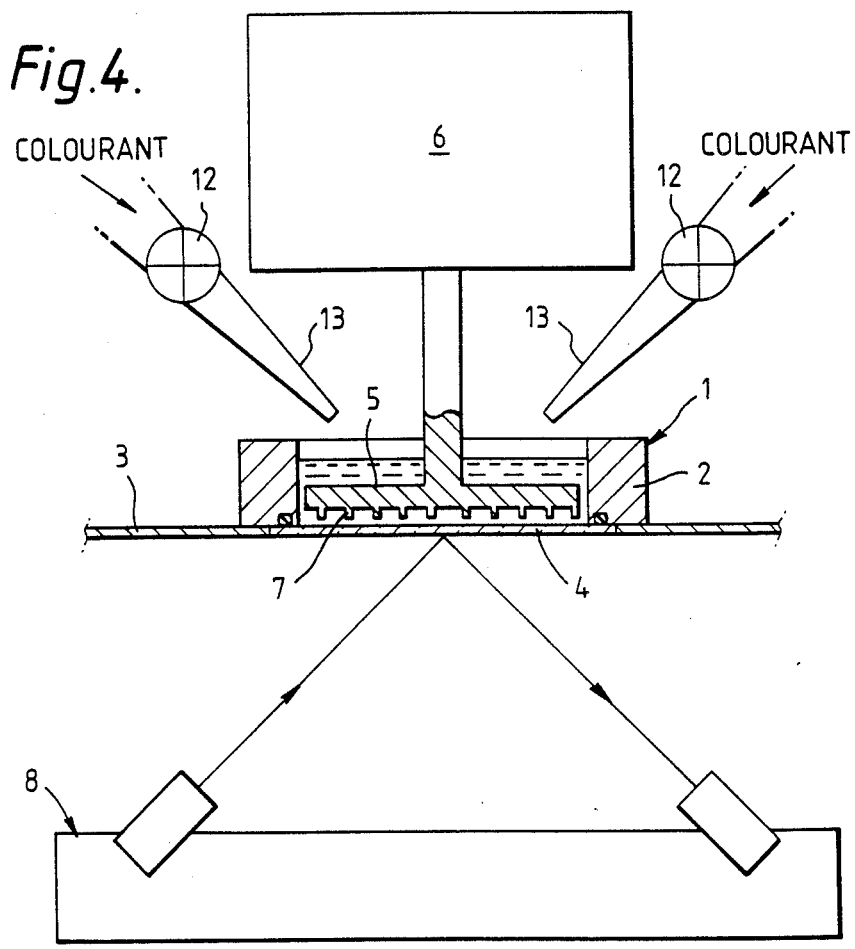
FIG. 4 is a schematic view of an apparatus in which colorants can be added during shearing.

Referring now to FIG. 4 this shows basically the same apparatus as in FIG. 1, and the same reference numerals have been used to designate corresponding parts. Additionally however a plurality of colorant dispensing valves 12 with nozzles 13 are shown for making colorant additions to the paint in the cell 1. This dispensing system can advantageously, as far as space saving is concerned, take the form described in UK Patent Application No. 8705482. As described in that Patent Application, a dispensing system comprises a circulating path for the paint to and from a reservoir, means for pressurising the paint to cause it to circulate around the path, a first valve means operable to divert the paint from the circulating path to a second valve means which is biased to a closed position and is openable by the hydraulic pressure of the paint to cause the liquid to be dispensed therefrom through a nozzle in the second valve means into the vessel 1. One such dispensing system is provided for each basic colour.

The first and second valve means need not be positioned adjacent each other but could be interconnected by a liquid feed line. The second valve means, i.e. the valves 12,13 can be designed as relatively slim valves and do not have to carry bulky acutating means. Consequently, a relatively large number of them can be disposed close together in an inverted conical form for feeding paint into the cell 1 with the nozzles directed towards the apex of the cone.

The addition of the colorants may be done in response to a request from a computer as a result of the colour measurements made by the spectrophotometer 8.

Figure 5A:
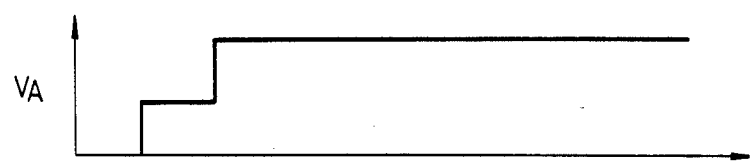
FIGS. 5a–5e show graphs explaining the method of using the apparatus of FIG. 4.
Figure 5B:
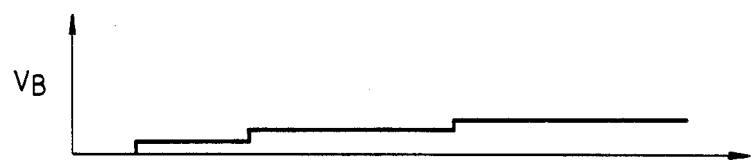
Figure 5C:
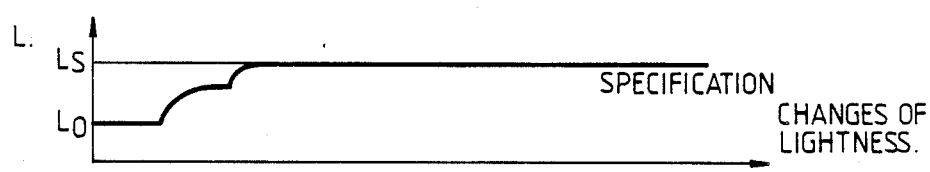
Figure 5D:
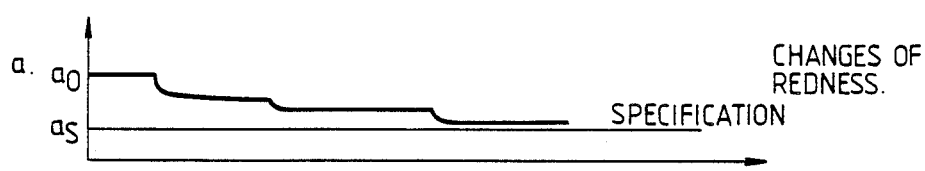
Figure 5E:
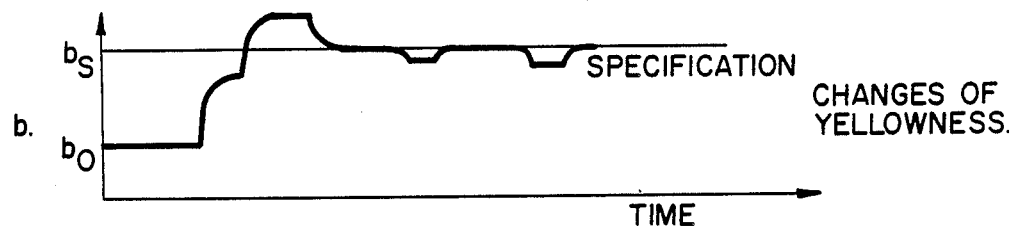

FIGS. 5a and 5b represents the volumes $V_A$ and $V_B$ of the added colorants A and B with time while the paint is being sheared and FIGS. 5C, 5D and 5E represent the corresponding changes in colour properties resulting from the colorant additions.

Figure 6:
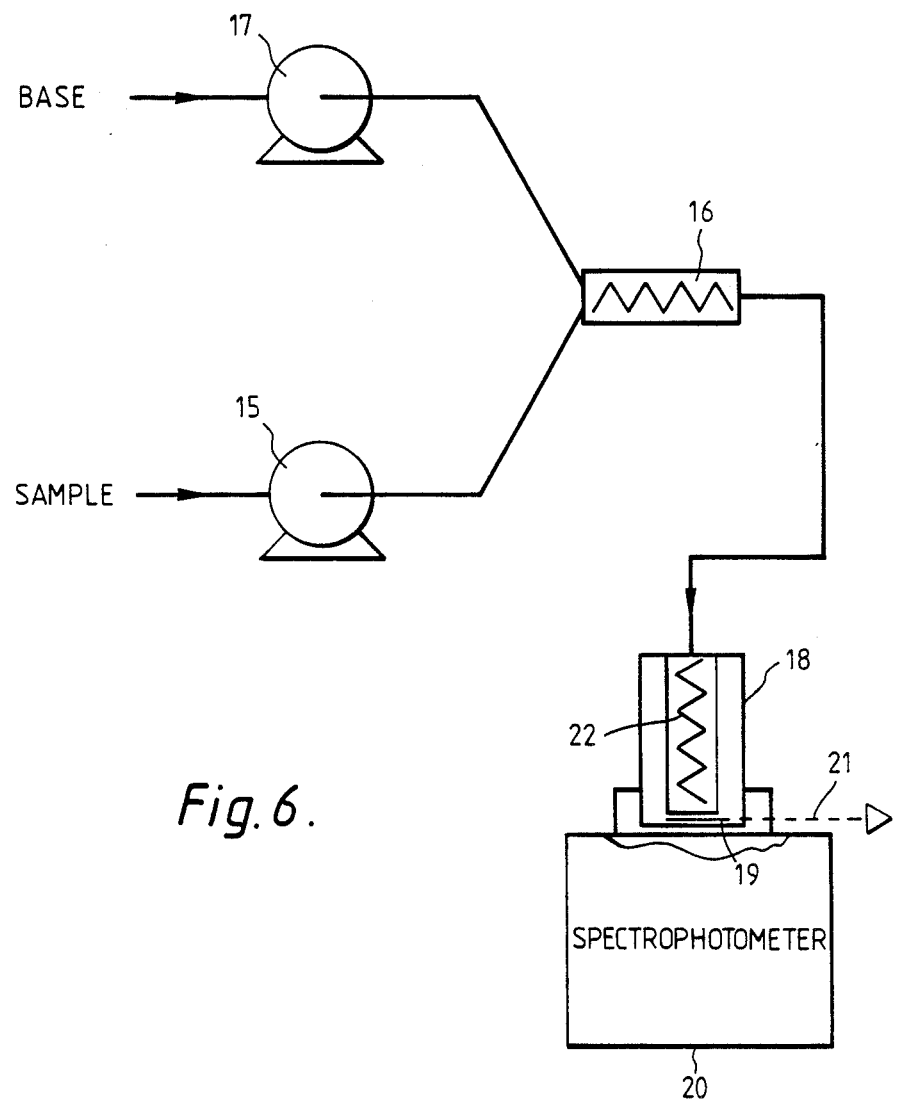
FIG. 6 is a schematic view of a further apparatus in accordance with the invention.

Referring now to FIG. 6, this shows a static shearing apparatus and also demonstrates the possibility of having an on-line colour measuring system.

A sample of paint is tapped off from the production line and is pumped via pump 15 to a mixer 16. At this point the sample may be mixed with a basic paint, e.g. white, which is pumped to the mixer 16 by pump 17. Alternatively the line via pump 17 can be used for another sample acquisition.

From the mixer 16, the sample flows under the pumping pressure to a cell 18 through which the sample flows. The cell 18 is in the form of a relatively small diameter tube having the paint inlet at one end and being closed off at the other end by a viewing window 19. A spectrophotometer 20 is positioned to make colour measurements through the window 19. The paint exits from a lateral outlet in the cell as indicated by dotted arrow 21.

Extending axially of the tube is a static shearing device 22 comprising a series of vanes or blades which extend transversely and obliquely of the tube axis. Such devices are already used in the paint mixing field and can be used as shearing devices providing that they and the tube have the appropriate relative dimensions and the paint is passed at a rate sufficient to achieve an appropriate shear rate of about $10^8$ reciprocal seconds.

The total cycle time of an apparatus as shown in FIG. 6 would be seconds rather than minutes. By adjustment of the axial position of the shearing device 22 the time the colour measurement is made after shear can be adjusted. Other factors which can be adjusted are shear rate, time of shear, temperature and flow rate.

We claim:

1. A method of measuring a colour property of wet paint comprising supplying a sample volume of liquid paint to a vessel, applying shearing forces to the sample volume in the vessel, and measuring the colour property of the sample volume while the sample is in the vessel and during the application of shearing forces and/or within a predetermined time after the cessation of the application of shearing forces.

2. A method according to claim 1, wherein turbulence is created in the sample volume simultaneously with the application of shearing forces.

3. A method according to claim 1, wherein the shearing forces applied produce a shear rate in the range $10^6$–$10^{10}$ reciprocal seconds.

4. A method according to claim 3, wherein the shearing force applied to the wet paint produces a shear rate of about $10^8$ reciprocal seconds.

5. A method according to claim 1 wherein the measurement of the colour property is made a predetermined time after the initiation of the shearing force and before the cessation thereof.

6. A method according to claim 1, wherein a series of measurements of the colour property are made both during the application of the shearing force and after the cessation of the application of the shearing force.

7. A method according to claim 6, wherein at least one measurement is also made prior to the initiation of the shearing force.

8. A method according to claim 1, wherein a colorant is added to the sample volume during shearing until the colour measurements made have a desired value.

9. Apparatus for carrying out the method of claim 1, comprising a vessel for holding a sample volume of paint, a device within the vessel for causing the sample volume to be subjected to shearing forces and measuring means arranged to measure a colour property of the sample volume in the vessel.

10. Apparatus according to claim 9, wherein said device comprises a rotatable disc disposed in said vessel and has protrusions on one surface thereof whereby in addition to causing shearing it also creates a turbulent flow in the sample volume.

11. Apparatus according to claim 10, wherein said protrusions are provided by a spiral rib configuration on said one surface.

12. Apparatus according to claim 10, wherein the measuring means includes a window in the vessel through which the colour property can be measured and said rotatable disc is disposed with its plane substantially parallel to said window and with said protrusions on the surface of the disc facing the window.

13. Apparatus according to claim 9 and including means for feeding colorant into said vessel.

14. Apparatus according to claim 9, wherein the vessel is of tubular form and the device comprises a stationary shearing member extending axially of the vessel, whereby the sample volume becomes sheared when it flows under pressure through the tubular member.

15. Apparatus according to claim 14, wherein the tubular vessel is provided with a window past which the sample volume flows after passing said shearing device and through which the colour property can be measured.

* * * * *